United States Patent
Kim et al.

(10) Patent No.: US 10,470,668 B2
(45) Date of Patent: Nov. 12, 2019

(54) CONTACTLESS CARDIOPULMONARY SIGNAL ESTIMATION METHOD AND APPARATUS

(71) Applicant: Electronics and Telecommunications Research Institute, Daejeon (KR)

(72) Inventors: Jung Bin Kim, Seoul (KR); Soon Young Eom, Daejeon (KR); Joung Myoun Kim, Daejeon (KR); Tae Jin Chung, Daejeon (KR); Jae Ick Choi, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 892 days.

(21) Appl. No.: 14/592,082

(22) Filed: Jan. 8, 2015

(65) Prior Publication Data
US 2015/0196205 A1    Jul. 16, 2015

(30) Foreign Application Priority Data
Jan. 10, 2014 (KR) .................. 10-2014-0003406

(51) Int. Cl.
| | | |
|---|---|---|
| *A61B 5/0205* | (2006.01) | |
| *A61B 5/113* | (2006.01) | |
| *A61B 5/11* | (2006.01) | |
| *A61B 5/00* | (2006.01) | |
| *A61B 5/08* | (2006.01) | |
| *A61B 5/024* | (2006.01) | |

(52) U.S. Cl.
CPC .......... *A61B 5/0205* (2013.01); *A61B 5/0816* (2013.01); *A61B 5/1102* (2013.01); *A61B 5/113* (2013.01); *A61B 5/1135* (2013.01); *A61B 5/7246* (2013.01); *A61B 5/024* (2013.01)

(58) Field of Classification Search
CPC ..... A61B 5/0205; A61B 5/1135; A61B 5/113; A61B 5/1102; A61B 5/0816; A61B 5/7246; A61B 5/024
See application file for complete search history.

(56) References Cited

U.S. PATENT DOCUMENTS

| | | | | |
|---|---|---|---|---|
| 5,347,843 | A * | 9/1994 | Orr ......................... | G01F 1/363 600/538 |
| 5,945,940 | A * | 8/1999 | Cuomo .................... | G01S 7/412 342/195 |
| 2005/0096589 | A1 * | 5/2005 | Shachar ............. | A61B 1/00158 604/95.01 |
| 2008/0074307 | A1 * | 3/2008 | Boric-Lubecke .... | A61B 5/0205 342/28 |
| 2009/0112113 | A1 * | 4/2009 | Mukkamala ........... | A61B 5/029 600/526 |
| 2012/0136232 | A1 | 5/2012 | Jeong et al. | |
| 2014/0148711 | A1 * | 5/2014 | Yang .................... | A61B 5/0205 600/484 |
| 2019/0230106 | A1 * | 7/2019 | Abbaszadeh ...... | G05B 23/0229 |

\* cited by examiner

*Primary Examiner* — Jacqueline Cheng
*Assistant Examiner* — Tho Q Tran
(74) *Attorney, Agent, or Firm* — William Park & Associates Ltd.

(57) ABSTRACT

A contactless cardiopulmonary signal estimation method and apparatus are provided. A cardiopulmonary signal estimation apparatus may estimate a cardiopulmonary signal of a user from a heartbeat signal and a respiratory signal of the user in response to movement of a chest based on a cardiopulmonary exercise of the user.

6 Claims, 7 Drawing Sheets

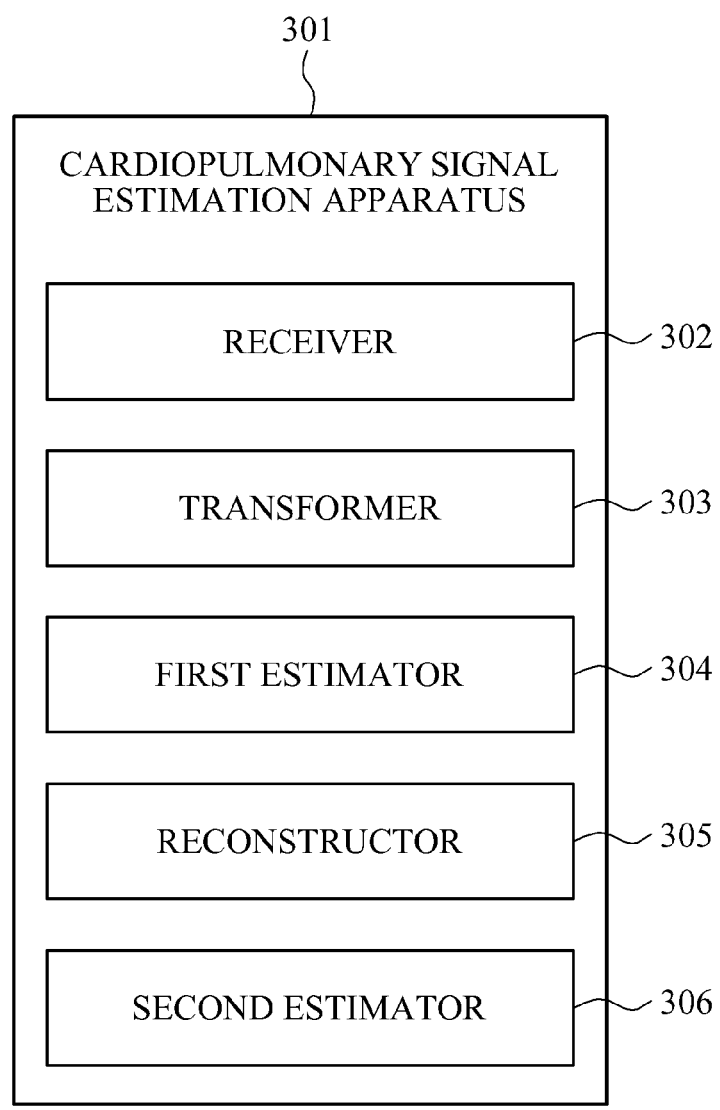

CONTACTLESS CARDIOPULMONARY SIGNAL ESTIMATION METHOD AND APPARATUS

CROSS-REFERENCE TO RELATED APPLICATION

This application claims the benefit of Korean Patent Application No. 10-2014-0003406, filed on Jan. 10, 2014, in the Korean Intellectual Property Office, the disclosure of which is incorporated herein by reference.

BACKGROUND

1. Field of the Invention

The present invention relates to a contactless cardiopulmonary signal estimation method and apparatus, and more particularly, to digital signal processing for more simply and accurately estimating a cardiopulmonary signal based on a characteristic of each of a heartbeat signal and a respiratory signal of a user.

2. Description of the Related Art

Recently, various methods are being proposed to monitor biosignals in an information technology (IT)-medicine convergence field including IT medical devices, ubiquitous health (u-health), and home care. In particular, various methods for measuring and monitoring cardiopulmonary signals in a contact manner or a contactless manner have been proposed.

To measure a cardiopulmonary signal, a continuous wave (CW) radar may be used. The CW radar may measure a Doppler shift amount of a reflection signal during periodical movement x(t) by a cardiopulmonary exercise in a state in which an object does not move, that is, there is no net velocity. To overcome a null point of a single receiver, a quadrature receiver with a phase difference of 90° may be used.

In an existing filter-based cardiopulmonary signal estimation scheme, a reception signal of a CW radar may be transformed to a digital signal, a heartbeat signal and a respiratory signal may be separated using a filter, and a cardiopulmonary signal may be estimated. However, because the filter is used to separate the heartbeat signal from the respiratory signal in the existing filter-based cardiopulmonary signal estimation scheme, operation complexity may be increased and an estimation error may occur.

Accordingly, a method of estimating a cardiopulmonary signal without using a filter to overcome the above disadvantage has been proposed. However, due to smearing and leakage, it may be difficult to detect signal components adjacent to a strong signal.

Additionally, a cardiopulmonary signal estimation method based on a RELAX algorithm to minimize the smearing and leakage has been proposed.

SUMMARY

An aspect of the present invention provides a cardiopulmonary signal estimation method and apparatus that may directly estimate a cardiopulmonary signal in a time domain using a brute-force search scheme based on a look-up table generated based on a correlation between estimation parameters, to minimize operation complexity and an estimation error caused by use of a filter.

Another aspect of the present invention provides a cardiopulmonary signal estimation method and apparatus that may sequentially estimate a heartbeat signal and a respiratory signal of a user in response to movement of a chest based on a cardiopulmonary exercise of the user, to have an efficient estimation performance corresponding to an ideal performance while minimizing complexity of estimation of the cardiopulmonary signal.

Another aspect of the present invention provides a cardiopulmonary signal estimation method and apparatus that may maximize a performance of an estimator required by a situation in which a cardiopulmonary signal is measured, by adjusting a size of a look-up table adaptively based on the situation.

According to an aspect of the present invention, there is provided a cardiopulmonary signal estimation method including: transforming a heartbeat signal and a respiratory signal of a user to a heartbeat signal and a respiratory signal in a discrete-time signal, in response to movement of a chest based on a cardiopulmonary exercise of the user; and directly estimating the heartbeat signal and the respiratory signal in the discrete-time signal in a time domain.

According to another aspect of the present invention, there is provided a cardiopulmonary signal estimation method including: receiving a cardiopulmonary signal in response to movement of a chest based on a cardiopulmonary exercise of a user, the cardiopulmonary signal including a heartbeat signal and a respiratory signal of the user; transforming the received cardiopulmonary signal to a discrete-time cardiopulmonary signal; setting, as noise, a heartbeat signal included in the discrete-time cardiopulmonary signal, and estimating a respiratory signal included in the discrete-time cardiopulmonary signal; reconstructing the discrete-time cardiopulmonary signal based on the estimated respiratory signal, to remove the respiratory signal from the discrete-time cardiopulmonary signal; and estimating the heartbeat signal based on the reconstructed cardiopulmonary signal.

According to another aspect of the present invention, there is provided a cardiopulmonary signal estimation apparatus including: a transformer to transform a heartbeat signal and a respiratory signal of a user to a heartbeat signal and a respiratory signal in a discrete-time signal, in response to movement of a chest based on a cardiopulmonary exercise of the user; and an estimator to estimate a cardiopulmonary signal of the user in a time domain based on the discrete-time signal.

According to another aspect of the present invention, there is provided a cardiopulmonary signal estimation apparatus including: a receiver to receive a cardiopulmonary signal in response to movement of a chest based on a cardiopulmonary exercise of a user, the cardiopulmonary signal including a heartbeat signal and a respiratory signal of the user; a transformer to transform the received cardiopulmonary signal to a discrete-time cardiopulmonary signal; a first estimator to set, as noise, a heartbeat signal included in the discrete-time cardiopulmonary signal, and to estimate a respiratory signal included in the discrete-time cardiopulmonary signal; a reconstructor to reconstruct the discrete-time cardiopulmonary signal based on an amplitude and a frequency component of the estimated respiratory signal, to remove the respiratory signal from the discrete-time cardiopulmonary signal; and a second estimator to estimate the heartbeat signal based on the reconstructed cardiopulmonary signal.

EFFECT

According to embodiments, a cardiopulmonary signal may be estimated directly in a time domain using a brute-force search scheme based on a look-up table generated based on a correlation between estimation parameters and thus, it is possible to minimize operation complexity and an estimation error caused by use of a filter.

Additionally, according to embodiments, a heartbeat signal and a respiratory signal of a user may be sequentially estimated in response to movement of a chest based on a cardiopulmonary exercise of the user and thus, it is possible to have an efficient estimation performance corresponding to an ideal performance while minimizing complexity of estimation of a cardiopulmonary signal.

Furthermore, according to embodiments, it is possible to maximize a performance of an estimator required by a situation in which a cardiopulmonary signal is measured, by adjusting a size of a look-up table adaptively based on the situation.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which:

FIG. 3 is a block diagram illustrating another example of a configuration of a cardiopulmonary signal estimation apparatus according to an embodiment;

DETAILED DESCRIPTION

Figure 1:
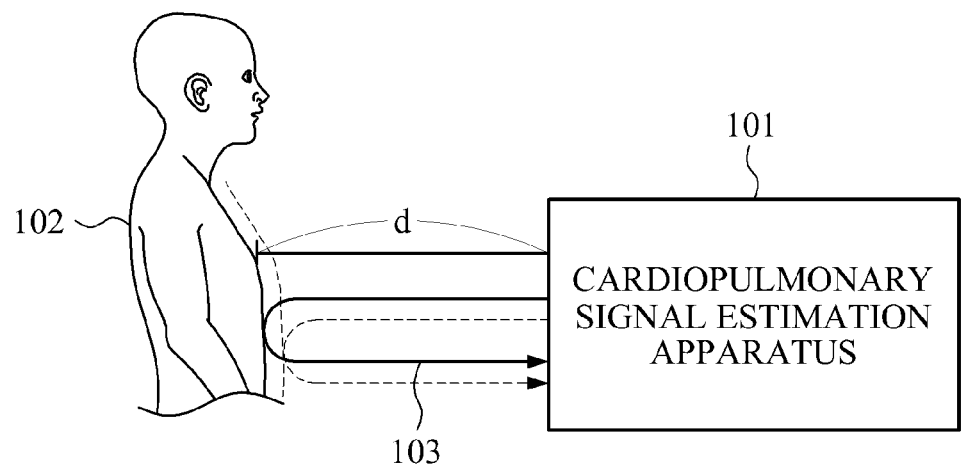
FIG. 1 is a diagram illustrating a cardiopulmonary signal estimation apparatus according to an embodiment.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a diagram illustrating a cardiopulmonary signal estimation apparatus 101 according to an embodiment. The cardiopulmonary signal estimation apparatus 101 may refer to an apparatus configured to measure a cardiopulmonary signal of a user without contacts, and may be more accurately estimate a cardiopulmonary signal of a user based on a characteristic of each of a respiratory signal and a heartbeat signal.

Referring to FIG. 1, the cardiopulmonary signal estimation apparatus 101 may estimate a cardiopulmonary signal of a user 102 without contacts. For example, the cardiopulmonary signal estimation apparatus 101 may receive a cardiopulmonary signal in response to movement of a chest based on a cardiopulmonary exercise of a user. The cardiopulmonary signal may include a heartbeat signal and a respiratory signal of the user. The heartbeat signal may refer to a signal generated by heartbeats of the user, and the respiratory signal may refer to a signal generated by pulmonary exercise of the user.

The cardiopulmonary signal estimation apparatus 101 may output a signal used to estimate a cardiopulmonary signal in a state in which the cardiopulmonary signal estimation apparatus 101 and the user 102 are separated from each other by a predetermined distance d. The output signal may be reflected from a chest of the user 102 back to the cardiopulmonary signal estimation apparatus 101. In FIG. 1, a cardiopulmonary signal 103 including a heartbeat signal and a respiratory signal of the user 102 may be input to the cardiopulmonary signal estimation apparatus 101.

The cardiopulmonary signal 103 may include a cardiopulmonary signal measured immediately when the output signal arrives at the user 102, and a cardiopulmonary signal having a difference between a distance from an expanded chest of the user 102 to the cardiopulmonary signal estimation apparatus 101 and a distance from a contracted chest of the user 102 to the cardiopulmonary signal estimation apparatus 101. For example, the cardiopulmonary signal estimation apparatus 101 may receive a cardiopulmonary signal having a difference in a distance based on expansion and contraction of the chest.

Additionally, the cardiopulmonary signal estimation apparatus 101 may perform sampling on the received cardiopulmonary signal at regular intervals, may normalize the cardiopulmonary signal, and may transform the normalized cardiopulmonary signal to a discrete-time cardiopulmonary signal. The cardiopulmonary signal estimation apparatus 101 may apply the discrete-time cardiopulmonary signal to a least-squares estimation scheme, and may accurately estimate a cardiopulmonary signal of the user 102 in a time domain.

The cardiopulmonary signal estimation apparatus 101 may sequentially estimate a respiratory signal and a heartbeat signal included in the received cardiopulmonary signal. For example, the cardiopulmonary signal estimation apparatus 101 may set, as noise, the heartbeat signal in the received cardiopulmonary signal, and may estimate the respiratory signal in the received cardiopulmonary signal. The cardiopulmonary signal estimation apparatus 101 may reconstruct the discrete-time cardiopulmonary signal based on the estimated respiratory signal, and may remove the respiratory signal from the cardiopulmonary signal. The cardiopulmonary signal estimation apparatus 101 may estimate the heartbeat signal based on the reconstructed cardiopulmonary signal.

The cardiopulmonary signal estimation apparatus 101 may transform a signal including a cardiopulmonary signal to a discrete-time signal. Additionally, the cardiopulmonary signal estimation apparatus 101 may estimate a cardiopulmonary signal from the discrete-time signal.

Figure 2:
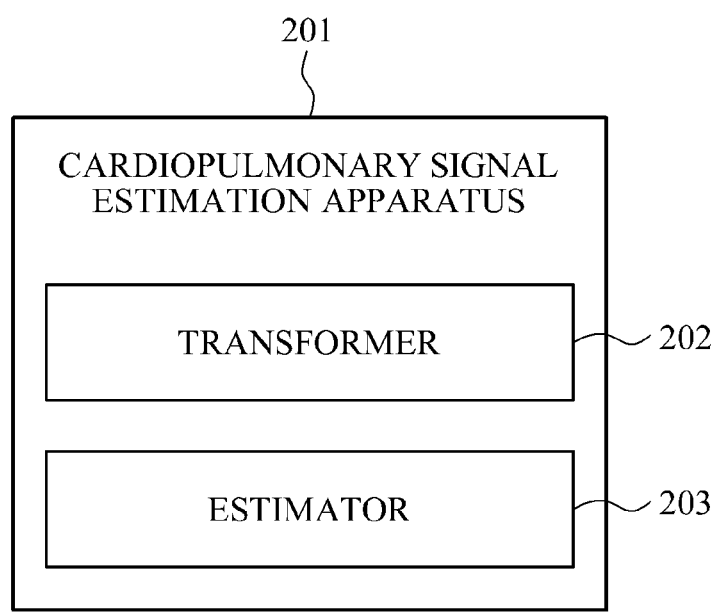
FIG. 2 is a block diagram illustrating an example of a configuration of a cardiopulmonary signal estimation apparatus according to an embodiment.

FIG. 2 is a block diagram illustrating a cardiopulmonary signal estimation apparatus 201 according to an embodiment.

Referring to FIG. 2, the cardiopulmonary signal estimation apparatus 201 may include a transformer 202, and an estimator 203.

The transformer 202 may receive a signal including a Doppler shift amount by movement of a chest based on a cardiopulmonary exercise of a user. The transformer 202 may perform sampling on the received signal at regular intervals, may normalize the signal, and may transform the normalized signal to a discrete-time signal. The estimator 203 may estimate a cardiopulmonary signal of the user from the discrete-time signal. The discrete-time signal may be represented as shown in Equation 1 below.

$$y_n = \cos\left[\frac{4\pi x_n}{\lambda} + \Phi\right] + j\sin\left[\frac{4\pi x_n}{\lambda} + \Phi\right] + v_n \quad \text{[Equation 1]}$$

In Equation 1, $y_n$ denotes a combination of a heartbeat signal and a respiratory signal in a discrete time. $\Phi$ denotes all residual phases accumulated in a circuit and a transmission path, and $v_n$ denotes a noise component.

The estimator 203 may apply a least-squares estimation scheme to the discrete-time signal. Additionally, the estimator 203 may estimate a cardiopulmonary signal of a user by applying the least-squares estimation scheme to the discrete-time signal. The least-squares estimation scheme may use a brute-force search scheme based on a look-up table generated based on a correlation between a heartbeat signal and a respiratory signal of a user by movement of a chest. The least-squares estimation scheme may be represented as shown in Equation 2 below.

$$\hat{m}_r, \hat{m}_h, \hat{\omega}_r, \hat{\omega}_h = \quad \text{[Equation 2]}$$
$$\min_{m_r, m_h, \omega_r, \omega_h} \sum_{n=0}^{N-1} \left( \begin{array}{c} y_n - \cos\left[\frac{4\pi x_n(m_r, m_h, \omega_r, \omega_h)}{\lambda} + \Phi\right] - \\ j\sin\left[\frac{4\pi x_n(m_r, m_h, \omega_r, \omega_h)}{\lambda} + \Phi\right] \end{array} \right)^2$$

The least-squares estimation scheme may not require approximation, and accordingly an error occurring in estimation of a cardiopulmonary signal of a user may be minimized. Additionally, in the least-squares estimation scheme, a filter may not be used and accordingly, complexity of an operation may be prevented from being increased and an estimation error may not occur due to use of the filter. In addition, the least-squares estimation scheme may prevent a nonconvergence problem from occurring when a cardiopulmonary signal is estimated based on an algorithm. Furthermore, a solution derived through the least-squares estimation scheme may have a global optimal solution.

Based on the above description, the least-squares estimation scheme may use a brute-force search scheme based on a look-up table. In other words, since the brute-force search scheme requires a large amount of an operation, an operation complexity may increase. To solve the above problem, the brute-force search scheme may be based on the look-up table. To reduce complexity, the brute-force search scheme may minimize a number of elements of the look-up table based on a correlation between estimation parameters, and a cardiopulmonary signal of a user may be searched for based on the minimized number of elements. The number of elements of the look-up table may be minimized based on a correlation between a respiratory signal and a heartbeat signal and accordingly, a size of the look-up table may be adjusted. For example, the look-up table may be written below.

A respiratory signal and a heartbeat signal may be represented by a function of $(m_r, m_h, \omega_r, \omega_h)$, and a number of elements in a set $\{(m_r, m_h, \omega_r, \omega_h)\}$ may be very limited. For example, a respiration rate of a user may be within a range of 0 beats per minute (bpm) to 100 bpm. The estimator 203 may set a range of respiration rates of a user from 0 bpm to 100 bpm as a measurement range, and may set a measurement resolution to 0.5 bpm. Based on the setting, the respiration rate of the user may have a set of about 200 elements. Similarly, the estimator 203 may set a range of heart rates of a user from 0 bpm to 200 bpm as a measurement range, and may set a measurement resolution to 0.5 bpm. Based on the setting, the heart rate of the user may have a set of about 400 elements.

Each of estimation parameters $m_r, m_h, \omega_r, \omega_h$ used to estimate a cardiopulmonary signal of a user may have elements $S_{m_r}, S_{m_h}, S_{\omega_r}, S_{\omega_h}$. Each of the estimation parameters $m_r, m_h, \omega_r, \omega_h$ may include a respiratory signal and a heartbeat signal to estimate the cardiopulmonary signal. Accordingly, estimation parameters may include, for example, a respiratory amplitude $m_r$ and a respiration rate $\omega_r$ of a respiratory signal, a heartbeat amplitude $m_h$ and a heart rate $\omega_h$ of a heartbeat signal.

For example, when the elements $S_{m_r}, S_{m_h}, S_{\omega_r}, S_{\omega_h}$ are included in each of the estimation parameters $m_r, m_h, \omega_r, \omega_h$, a look-up table including estimation parameters $\hat{m}_r, \hat{m}_h, \hat{\omega}_r, \hat{\omega}_h$ having vector values may have a total of $S_{m_r} \times S_{m_h} \times S_{\omega_r} \times S_{\omega_h}$ elements. In other words, a value of $S_{m_r} \times S_{m_h} \times S_{\omega_r} \times S_{\omega_h}$ may indicate that $S_{m_r} \times S_{m_h} \times S_{\omega_r} \times S_{\omega_h}$ coordinates are to be compared to perform a brute-force search scheme.

Due to a characteristic of each of a respiratory signal and a heartbeat signal, each of the elements $S_{m_r}, S_{m_h}, S_{\omega_r}, S_{\omega_h}$ may have a small value. For example, when the least-squares estimation scheme represented by Equation 2 is performed based on a look-up table with a small value, the estimator 203 may estimate a more accurate cardiopulmonary signal, instead of increasing complexity. Additionally, the above method may be used to easily detect a cardiopulmonary signal of a user in an emergency situation.

Additionally, the estimator 203 may reduce a size of the set $\{(m_r, m_h, \omega_r, \omega_h)\}$ based on a correlation between the respiratory signal and the heartbeat signal. For example, a value of $S_{m_r} \times S_{m_h} \times S_{\omega_r} \times S_{\omega_h}$ indicating a number of elements in the set $\{(m_r, m_h, \omega_r, \omega_h)\}$ may be greatly applied based on a value applied by an application used to estimate a cardiopulmonary signal of a user and accordingly, the estimator 203 may reduce the size of the $\{(m_r, m_h, \omega_r, \omega_h)\}$.

For example, a respiration rate may increase, as a heart rate increases. Additionally, the heart rate may increase, as the respiration rate increases. Furthermore, a user may rarely breathe when a heartbeat is stopped.

Similarly, a respiratory amplitude and a respiration rate of the respiratory signal may correlate with a heart rate amplitude and a heart rate of the heartbeat signal. The estimator 203 may remove elements indicating cases that are unlikely to actually occur from the set of elements $\{(m_r, m_h, \omega_r, \omega_h)\}$ in the look-up table, based on a correlation between a heartbeat signal and a respiratory signal that are transformed in a time domain. For example, a case of respiration during a cardiac standstill, represented by elements $\{(m_r, 0, \omega_r, 0)\}$ may be highly unlikely to occur and accordingly, the elements $\{(m_r, 0, \omega_r, 0)\}$ may be removed from the look-up table.

The estimator 203 may significantly reduce complexity for estimating a cardiopulmonary signal by removing an element indicating a case that is not likely to actually occur.

FIG. 3 is a block diagram illustrating a cardiopulmonary signal estimation apparatus 301 according to an embodiment.

Referring to FIG. 3, the cardiopulmonary signal estimation apparatus 301 includes a receiver 302, a transformer 303, a first estimator 304, a reconstructor 305, and a second estimator 306.

The receiver 302 may receive a signal that is Doppler-shifted and that includes a cardiopulmonary signal, in response to movement of a chest based on a cardiopulmonary exercise of a user. The cardiopulmonary signal may include a heartbeat signal and a respiratory signal of the user.

The transformer 303 may transform the received signal to a discrete-time signal. The transformer 303 may perform sampling on the received signal at regular intervals, may normalize the signal, and may transform the normalized signal to the discrete-time signal.

The first estimator 304 may set, as noise, a heartbeat signal in a cardiopulmonary signal included in the discrete-time signal, and may estimate a respiratory signal in the cardiopulmonary signal. For example, the first estimator 304 may estimate a respiratory signal from a discrete-time signal including a cardiopulmonary signal, based on Equation 3 shown below.

$$\hat{m}_r, \hat{\omega}_r = \min_{m_r, \omega_r} \sum_{n=0}^{N-1} \left( \begin{array}{c} y_n - \cos\left[\frac{4\pi x_{n,r}(m_r, \omega_r)}{\lambda} + \Phi\right] - \\ j\sin\left[\frac{4\pi x_{n,r}(m_r, \omega_r)}{\lambda} + \Phi\right] \end{array} \right)^2$$ [Equation 3]

The first estimator 304 may estimate a respiratory amplitude $\hat{m}_r$ and a respiration rate $\hat{\omega}_r$ of a respiratory signal with a vector value. For example, the first estimator 304 may set, as noise, a heartbeat signal in a cardiopulmonary signal included in a discrete-time signal. The heartbeat signal, and the cardiopulmonary signal may be represented by $x_{n,h}(m_h, \omega_h)$, and $x_n(m_r, m_h, \omega_r, \omega_h) = x_{n,r}(m_r, \omega_r) + x_{n,h}(m_h, \omega_h)$, respectively. In this example, the cardiopulmonary signal may include estimation parameters. Additionally, the first estimator 304 may estimate a respiratory signal other than the heartbeat signal set as noise. A magnitude of the heartbeat signal may typically be greater than at least 100 times that of the respiratory signal. Accordingly, the first estimator 304 may estimate a respiratory signal by setting, as noise, a heartbeat signal in a cardiopulmonary signal included in a discrete-time signal, without degradation in performance.

The first estimator 304 may estimate the respiratory signal from the cardiopulmonary signal included in the discrete-time signal, using a brute-force search scheme based on a look-up table generated based on a respiratory amplitude and a respiration rate of the respiratory signal. The look-up table may include a set of elements $\{(m_r, \omega_r)\}$. For example, the first estimator 304 may estimate a respiratory signal of a user based on a look-up table including only respiratory signals.

The reconstructor 305 may reconstruct the cardiopulmonary signal based on the estimated respiratory signal. For example, the reconstructor 305 may reconstruct the cardiopulmonary signal based on the estimated respiratory signal, as shown in Equation 4 below, and may remove the respiratory signal from the cardiopulmonary signal.

$$\tilde{x}_n = x_{n,h} + \hat{x}_{n,r} = m_k \sin(\omega_h \Delta_T n) + \hat{m}_r \sin(\hat{\omega}_r \Delta_T n)$$ [Equation 4]

In Equation 4, $\Delta_t$ denotes a sampling interval, and $\hat{m}_r$ denotes an amplitude of the respiratory signal estimated based on Equation 3. Additionally, $\hat{\omega}_r$ denotes a frequency component of the respiratory signal estimated based on Equation 3. The reconstructor 305 may reconstruct the cardiopulmonary signal based on the amplitude and frequency component of the estimated respiratory signal, and may remove the respiratory signal from the cardiopulmonary signal.

The second estimator 306 may estimate the heartbeat signal based on the reconstructed cardiopulmonary signal. The estimated heartbeat signal may be represented as shown in Equation 5 below.

$$\hat{m}_h, \hat{\omega}_h = \min_{m_h, \omega_h} \sum_{n=0}^{N-1} \left( \begin{array}{c} y_n - \cos\left[\frac{4\pi \tilde{x}_n(\hat{m}_r, m_h, \hat{\omega}_r, \omega_h)}{\lambda} + \Phi\right] - \\ j\sin\left[\frac{4\pi \tilde{x}_n(\hat{m}_r, m_h, \hat{\omega}_r, \omega_h)}{\lambda} + \Phi\right] \end{array} \right)^2$$ [Equation 5]

The second estimator 306 may estimate a heartbeat amplitude $\hat{m}_h$ and a heart rate $\hat{\omega}_h$ of the heartbeat signal, based on the respiratory amplitude and the respiration rate of the respiratory signal estimated by the first estimator 304.

The second estimator 306 may estimate the heartbeat signal, using a brute-force search scheme based on a look-up table. A size of the look-up table may be adjusted based on a correlation between the heartbeat amplitude of the heartbeat signal and the respiratory amplitude of the respiratory signal and a correlation between the heart rate of the heartbeat signal and the respiration rate of the respiratory signal.

The cardiopulmonary signal estimation apparatus 301 may sequentially estimate the respiratory signal and the heartbeat signal and accordingly, a size of the look-up table may be minimized. For example, when the respiratory signal and the heartbeat signal are sequentially estimated, the cardiopulmonary signal estimation apparatus 301 may reduce complexity for estimating the heartbeat signal, because a number of elements of the look-up table required to be compared when a brute-force search scheme is applied, is reduced to a value of $(S_{m_r} \times S_{m_h}) + (S_{\omega_r} \times S_{\omega_h})$.

Figure 4A:
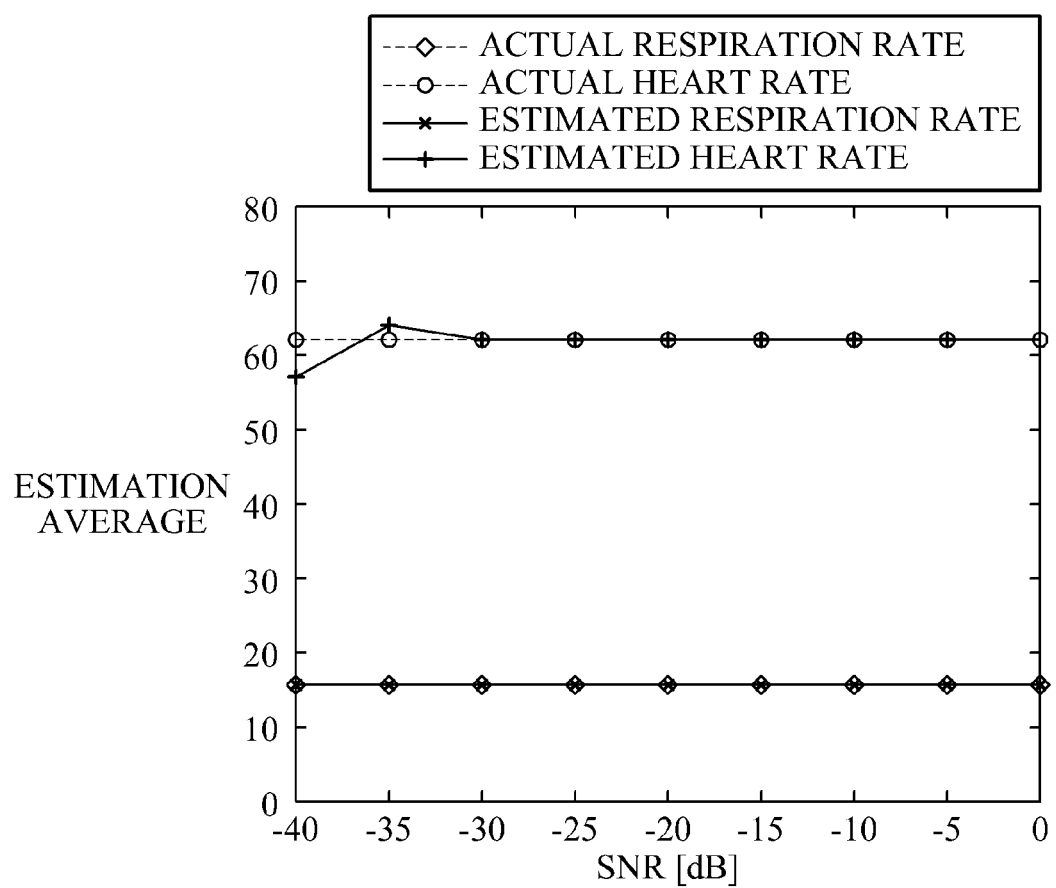
FIGS. 4A and 4B are graphs illustrating a cardiopulmonary signal estimated using a cardiopulmonary signal estimation apparatus according to an embodiment.
Figure 4B:
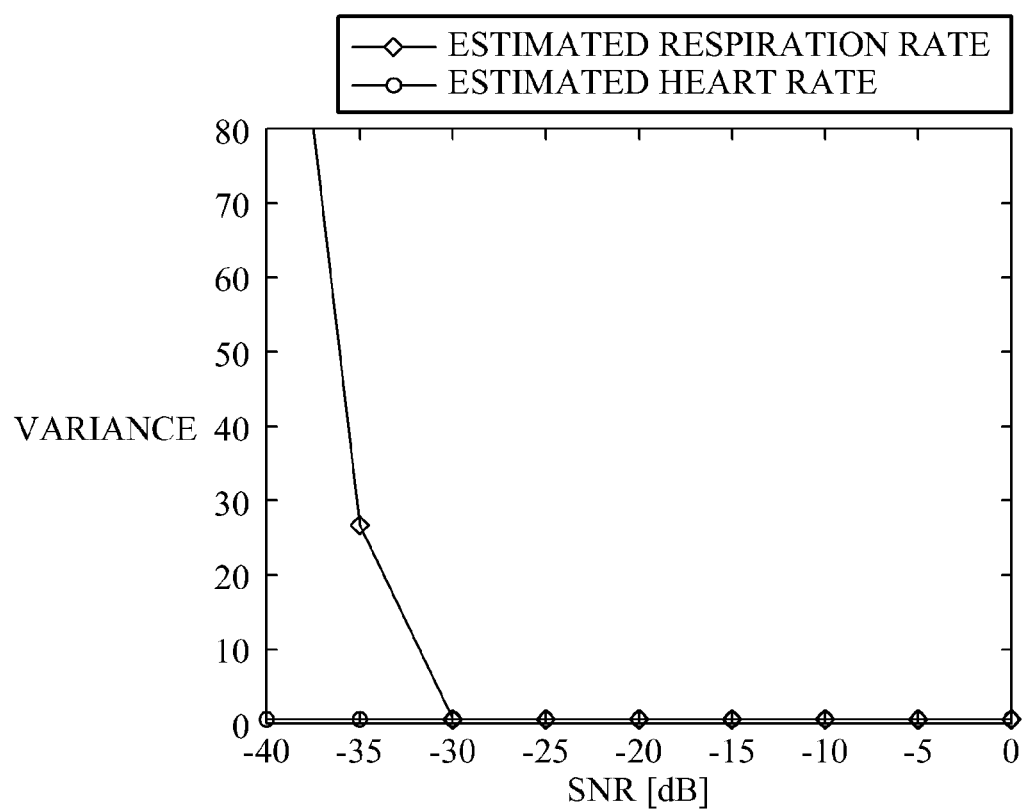

FIGS. 4A and 4B illustrate graphs of a cardiopulmonary signal estimated using a cardiopulmonary signal estimation apparatus according to an embodiment.

FIGS. 4A and 4B illustrate an estimation average and estimation variance (*variance of a cardiopulmonary signal estimated through a cardiopulmonary signal estimation process, respectively. An actual heart rate and an actual respiration rate of a user are set to 62 bpm and 16 bpm, and are measured 100 times. Additionally, a central frequency of a radar transmission signal is set to 2.3 gigahertz (GHz), and a sampling time and a measurement time are set to 0.01 second (s) and 30 s for each estimation, respectively.

Referring to FIGS. 4A and 4B, an efficient estimation performance corresponding to an ideal performance of an estimator may be obtained at a respiration rate corresponding to a signal-to-noise ratio (SNR) that is less than or equal to −40 decibels (dB), and a heart rate corresponding to an SNR that is equal to or greater than −30 dB. In other words, the estimation average and variance of FIGS. 4A and 4B may be unbiased, and the variance may be zero.

Figure 5:
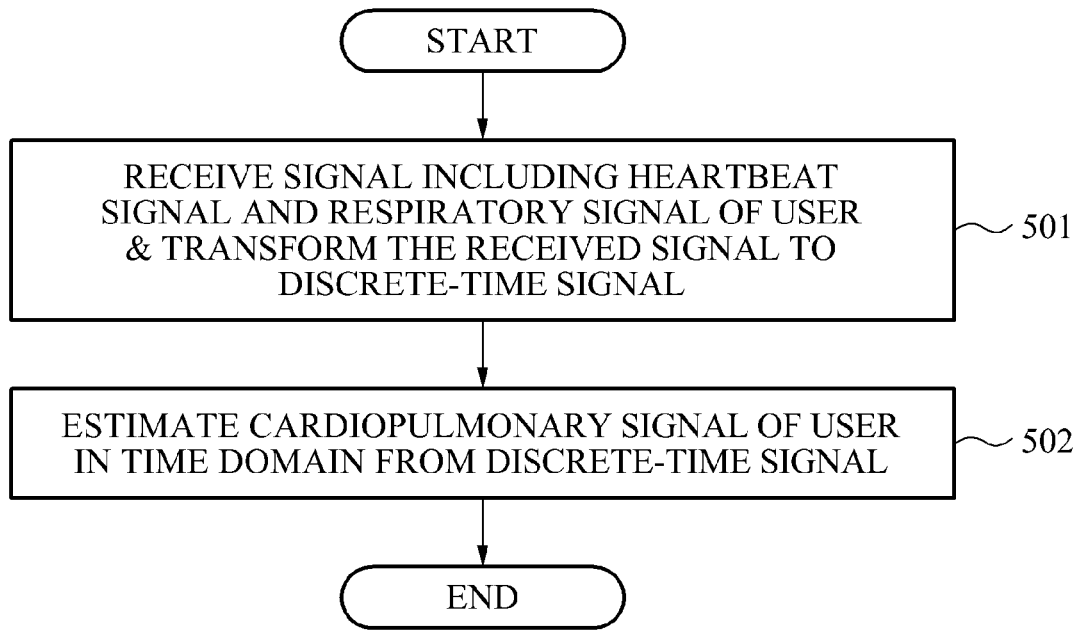
FIG. 5 is a flowchart illustrating an example of a cardiopulmonary signal estimation method according to an embodiment.

FIG. 5 illustrates an example of a cardiopulmonary signal estimation method according to an embodiment.

Referring to FIG. 5, in operation 501, a cardiopulmonary signal estimation apparatus may receive a signal in response to movement of a chest based on a cardiopulmonary exercise of a user. The signal may include a heartbeat signal and a respiratory signal of the user. In operation 501, the signal may be sampled at regular intervals, may be normalized, and may be transformed to a discrete-time signal.

In operation 502, the cardiopulmonary signal estimation apparatus may estimate a cardiopulmonary signal of the user in a time domain from the discrete-time signal. To estimate a heartbeat signal and a respiratory signal, the cardiopulmonary signal estimation apparatus may apply a brute-force search scheme of a least-squares estimation scheme. The cardiopulmonary signal estimation apparatus may estimate the cardiopulmonary signal of the user by applying a heartbeat signal and a respiratory signal in the discrete-time signal to the brute-force search scheme.

The cardiopulmonary signal estimation apparatus may adjust a size of a look-up table based on a correlation between the respiratory signal and the heartbeat signal. The cardiopulmonary signal estimation apparatus may change the size of the look-up table adaptively based on a situation in which a cardiopulmonary signal is required to be estimated. In an example, when an amplitude of respiration of a user is provided in advance through advance invention, the cardiopulmonary signal estimation apparatus may remove an element used to estimate a value of the amplitude from the look-up table.

In another example, when monitoring of a cardiopulmonary signal is required to observe a change in a physical condition of people, the cardiopulmonary signal estimation apparatus may remove a portion of or all of elements corresponding to an emergency situation from the look-up table.

Accordingly, the cardiopulmonary signal estimation apparatus may maximize a performance of an estimator required depending on circumstances by adaptively changing the size of the look-up table. For example, when quick estimation is required rather than accurate estimation, the cardiopulmonary signal estimation apparatus may minimize the size of the look-up table, and may maximize a performance of an estimator required depending on circumstances, that is, quick estimation. An element used to determine the size of the look-up table may include, for example, a resolution, an estimation mode (for daily life and/or for hospital), existence or nonexistence of advance information, and the like. The estimator may be used to estimate a cardiopulmonary signal of a user.

Figure 6:
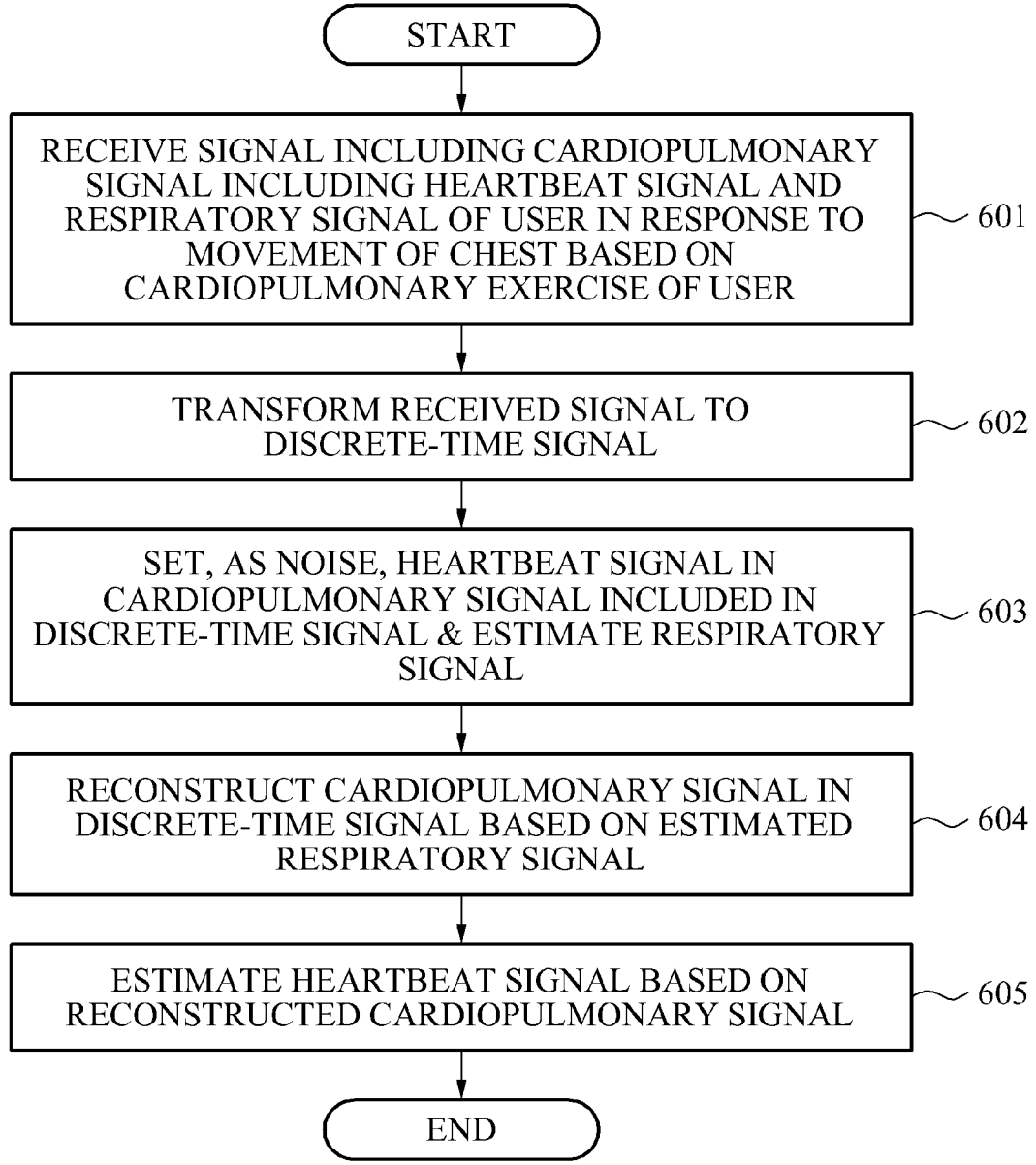
FIG. 6 is a flowchart illustrating another example of a cardiopulmonary signal estimation method according to an embodiment.

FIG. 6 illustrates another example of a cardiopulmonary signal estimation method according to an embodiment.

Referring to FIG. 6, in operation 601, a cardiopulmonary signal estimation apparatus may receive a signal including a cardiopulmonary signal, in response to movement of a chest based on a cardiopulmonary exercise of a user. The cardiopulmonary signal may include a heartbeat signal and a respiratory signal of the user.

In operation 602, the cardiopulmonary signal estimation apparatus may transform the received signal to a discrete-time signal.

In operation 603, the cardiopulmonary signal estimation apparatus may set, as noise, a heartbeat signal in a cardiopulmonary signal included in the discrete-time signal, and may estimate a respiratory signal in the cardiopulmonary signal included in the discrete-time signal. For example, the cardiopulmonary signal estimation apparatus may set, as noise, a heartbeat signal having a magnitude greater than at least 100 times that of a respiratory signal. Additionally, the cardiopulmonary signal estimation apparatus may estimate a respiratory signal other than the heartbeat signal set as noise.

In operation 604, the cardiopulmonary signal estimation apparatus may remove the respiratory signal from the cardiopulmonary signal in the discrete-time signal, based on the estimated respiratory signal. To remove the respiratory signal from the cardiopulmonary signal in the discrete-time signal, the cardiopulmonary signal estimation apparatus may reconstruct the cardiopulmonary signal in the discrete-time signal based on an amplitude and a frequency component of the estimated respiratory signal.

In operation 605, the cardiopulmonary signal estimation apparatus may estimate the heartbeat signal based on the reconstructed cardiopulmonary signal.

The cardiopulmonary signal estimation apparatus may estimate the cardiopulmonary signal of the user based on the estimated respiratory signal and the estimated heartbeat signal. The cardiopulmonary signal estimation apparatus may estimate the cardiopulmonary signal using a brute-force search scheme based on a look-up table generated based on a correlation between a respiratory amplitude and a respiration rate of the respiratory signal and a heartbeat amplitude and a heart rate of the heartbeat signal (*a correlation between a respiratory amplitude of the respiratory signal and a heartbeat amplitude of the heartbeat signal, and a correlation between a respiration rate of the respiratory signal and a heart rate of the heartbeat signal. The cardiopulmonary signal estimation apparatus may sequentially estimate the respiratory signal and the heartbeat signal and accordingly, a number of elements in the look-up table used to estimate the cardiopulmonary signal may be minimized to a value of $(S_{m_r} \times S_{m_h}) + (S_{\omega_r} \times S_{\omega_h})$.

According to embodiments, a cardiopulmonary signal estimation apparatus may sequentially estimate a respiratory signal and a heartbeat signal and accordingly, it is possible to greatly reduce complexity of estimation. Additionally, the cardiopulmonary signal estimation apparatus may have an efficient estimation performance corresponding to an ideal performance of an estimator.

Additionally, according to embodiments, a cardiopulmonary signal estimation apparatus may directly estimate a cardiopulmonary signal of a user in a time domain and accordingly, an approximation process may not be required, thereby reducing an error. In addition, because the cardiopulmonary signal estimation apparatus may not use a filter to estimate a cardiopulmonary signal, an estimation error may not occur and complexity may be prevented from being increased due to use of the filter. Moreover, a global optimal solution may be derived.

The above-described embodiments of the present invention may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A cardiopulmonary signal estimation method performed by a cardiopulmonary signal estimation apparatus, the cardiopulmonary signal estimation apparatus comprising one or more processors configured to execute:

program code that transforms a cardiopulmonary signal of a user that includes a heartbeat signal and a respiratory signal to a discrete-time signal, the cardiopulmonary signal being received when a chest of the user moves based on a cardiopulmonary exercise of the user, wherein the cardiopulmonary signal is received from a continuous wave radar sensor measuring movement of the user's chest during cardiopulmonary exercise;

program code that estimates a cardiopulmonary signal of the user in a time domain based on the discrete-time signal;

program code that estimates the cardiopulmonary signal based on a look-up table generated based on a correlation between the heartbeat signal and the respiration signal of the user due to the movement of the chest, and;

program code that adjusts a size of the look-up table when an element of the look-up table indicating a respiration or cardiac case that is unlikely to occur is removed;

wherein the one of more processors estimate the cardiopulmonary signal of the user in the time domain by applying the discrete-time signal to a least-squares estimation scheme that uses a brute-force search scheme based on the look-up table generated based on a correlation between the heartbeat signal and the respiratory signal received by movement of the chest.

2. The cardiopulmonary signal estimation method of claim 1, wherein the look-up table is generated based on at least one of a correlation between a respiratory amplitude and a respiration rate of the respiratory signal and a heartbeat amplitude and a heart rate of the heartbeat signal, a correlation between a respiratory amplitude of the respiratory signal and a heartbeat amplitude of the heartbeat signal, and a correlation between a respiration rate of the respiratory signal and a heart rate of the heartbeat signal.

3. The cardiopulmonary signal estimation method of claim 1, wherein a number of elements of the look-up table is minimized based on the correlation between the heartbeat signal and the respiratory signal.

4. A cardiopulmonary signal estimation apparatus, comprising:
one or more processors configured to execute:

program code that transforms a cardiopulmonary signal of a user that includes a heartbeat signal and a respiratory signal to a discrete-time signal, the cardiopulmonary signal being received when a chest moves based on a cardiopulmonary exercise of the user wherein the cardiopulmonary signal is received from a continuous wave radar sensor measuring movement of the user's chest during cardiopulmonary exercise;

program code that estimates a cardiopulmonary signal of the user in a time domain based on the discrete-time signal;

program code that estimates the cardiopulmonary signal based on a look-up table generated based on the correlation between the heartbeat signal and the respiration signal of the user due to the movement of the chest;

program code that adjusts a size of the look-up table when an element of the look-up table indicating a respiration or cardiac case that is unlikely to occur is removed;

wherein the one or more processors estimate the cardiopulmonary signal of the user in the time domain by applying the discrete-time signal to a least-squares estimation scheme that uses a brute-force search scheme based on the look-up table generated based on a correlation between the heartbeat signal and the respiratory signal received by movement of the chest.

5. The cardiopulmonary signal estimation apparatus of claim 4, wherein the look-up table is generated based on at least one of a correlation between a respiratory amplitude and a respiration rate of the respiratory signal and a heartbeat amplitude and a heart rate of the heartbeat signal, a correlation between a respiratory amplitude of the respiratory signal and a heartbeat amplitude of the heartbeat signal, and a correlation between a respiration rate of the respiratory signal and a heart rate of the heartbeat signal.

6. The cardiopulmonary signal estimation apparatus of claim 4, wherein a number of elements of the look-up table is minimized based on the correlation between the heartbeat signal and the respiratory signal.

\* \* \* \* \*